(12) United States Patent  (10) Patent No.: US 9,161,711 B2
Jallon et al.  (45) Date of Patent: Oct. 20, 2015

(54) SYSTEM AND METHOD FOR DETECTING AN EPILEPTIC SEIZURE IN A PRONE EPILEPTIC PERSON

(75) Inventors: Pierre Jallon, Grenoble (FR); Stéphane Bonnet, Lyons (FR)

(73) Assignees: MOVEA, Grenoble (FR); COMMISSARIAT A L'ENERGIE ATOMIQUE ET AUX ALTERNATIVES, Paris (FR)

( * ) Notice: Subject to any disclaimer, the term of this patent is extended or adjusted under 35 U.S.C. 154(b) by 644 days.

(21) Appl. No.: 13/391,239

(22) PCT Filed: Aug. 19, 2009

(86) PCT No.: PCT/EP2009/060740
§ 371 (c)(1),
(2), (4) Date: Mar. 19, 2012

(87) PCT Pub. No.: WO2011/020504
PCT Pub. Date: Feb. 24, 2011

(65) Prior Publication Data
US 2012/0165705 A1    Jun. 28, 2012

(51) Int. Cl.
*A61B 5/11* (2006.01)
*A61B 5/00* (2006.01)
(Continued)

(52) U.S. Cl.
CPC ............. *A61B 5/1118* (2013.01); *A61B 5/4094* (2013.01); *G06K 9/00536* (2013.01); *G06K 9/6297* (2013.01); *A61B 5/7264* (2013.01); *A61B 2562/0219* (2013.01)

(58) Field of Classification Search
CPC .. A61B 5/1118; A61B 5/4094; A61B 5/7264; A61B 2562/0219; G06K 9/00536; G06K 9/6297
USPC ......................................................... 600/595
See application file for complete search history.

(56) References Cited

U.S. PATENT DOCUMENTS

| 6,212,510 B1 | 4/2001 | Brand | |
| 2009/0062696 A1* | 3/2009 | Nathan et al. | 600/595 |
| 2009/0318779 A1* | 12/2009 | Tran | 600/301 |
| 2013/0245502 A1* | 9/2013 | Lange et al. | 600/595 |

FOREIGN PATENT DOCUMENTS

EP    2 023 268 A1    2/2009

OTHER PUBLICATIONS

Jin He et al.: "Real-time Daily Activity Classification with Wireless Sensor Networks using Hidden Markov Model", Aug. 1, 2007, pp. 3192-3195.

(Continued)

*Primary Examiner* — Sean Dougherty
*Assistant Examiner* — Michael C Stout
(74) *Attorney, Agent, or Firm* — Stroock & Stroock & Lavan LLP

(57) ABSTRACT

A system for detecting an epileptic seizure in a prone person, comprising:
    at least one motion sensor with at least one measurement axis having fastening means for securing said motion sensor to said person;
    first means for determining a first probability of at least a first state transition diagram of the nocturnal activity of a prone person with respect to data representing the measurement signals of the motion sensor, said first diagram comprising predetermined probabilities of oriented transitions between two different or identical states, the probabilities of the states of said first diagram being predetermined; and
    second means for determining a second probability of at least a second state transition diagram for an epileptic seizure with respect to data representing the measurement signals of the motion sensor, said second diagram comprising predetermined probabilities of oriented transitions between two different or identical states, the probabilities of the states of said second diagram being predetermined.

16 Claims, 1 Drawing Sheet

(51) Int. Cl.
*G06K 9/00* (2006.01)
*G06K 9/62* (2006.01)

(56) References Cited

OTHER PUBLICATIONS

Nijsen T M E et al.: "Detection of Subtle Nocturnal Motor Activity From 3-D Accelerometry Recordings in Epilepsy Patients", Nov. 1, 2007, pp. 2070-2081.

Becq G et al.: "Collection and Exploratory Analysis of Attitude Sensor Data in an Epilepsy Monitoring Unit", Aug. 22, 2007, pp. 2775-2778.

International Search Report and Written Opinion mailed Apr. 5, 2010, issued in priority International Application No. PCT/EP2009/060740.

* cited by examiner

SYSTEM AND METHOD FOR DETECTING AN EPILEPTIC SEIZURE IN A PRONE EPILEPTIC PERSON

CROSS-REFERENCE TO RELATED APPLICATION

This application is a national phase application under 35 U.S.C. §371 of PCT/EP2009/060740, filed Aug. 19, 2009, the entire contents of which are expressly incorporated herein by reference.

BACKGROUND

1. Field of the Invention

The present invention relates to a system and method for detecting an epileptic seizure in a prone epileptic person.

Epileptic seizures are caused by dysfunctions of the brain which may be manifested in various ways. This disorder affects between 0.5% and 1% of the population. 70% of these patients can control their epileptic seizures by using antiepileptic medication. For the other 30% of patients, surgery may be envisaged to remove the epileptic region, in other words the parts of the brain that trigger these seizures, in order to ensure that the patient has no more seizures.

Many of the symptoms of an epileptic seizure are motor symptoms. These symptoms can be recorded and analyzed using various devices such as video or motion sensors, in order to determine the nature of a patient's seizure or detect a seizure for reasons of safety.

2. Description of the Related Art

There are known video processing methods for quantifying the motor activity of a patient during a seizure. For this purpose, markers are placed on the patient. The main advantage of this type of method is that cameras are already in use in most hospital rooms. The problems associated with these methods are due to the fact that it is difficult to analyze movement automatically from a two-dimensional image, and uncertainties can arise if the marker disappears from the field of view. Furthermore, these types of method can only be used in a room where a camera is available.

Another approach to the motor characterization of epileptic seizures is the use of inertial/magnetic sensors. These sensors have made it possible to extract relevant data concerning human movements by the processing of multidimensional signals. Many applications have thus been developed using these low-cost, non-invasive sensors. The best-known of these is undoubtedly the analysis of posture and walk, as described for example in "A magnetometer-based approach for studying human movements", by S. Bonnet and R. Heliot, IEEE Transactions on Biomedical Engineering, vol. 54, no. 7, 2007, which proposes a 3D magnetometer-based process for the real-time evaluation of an inclination of the body to detect movements such as a change of position from seated to standing. The characterization of movements caused by neurological factors has also been investigated: for example, accelerometers have been used for Parkinson's disease and the detection of hand tremors, as described, respectively, in "The measuring set and signal processing method for the characterization of human hand tremor," by A. Chwaleba, J. Jakubowski and K. Kwiatos, CADSM, 2003, and "Triaxial accelerometry: a method for quantifying tremor and ataxia," by J. D. Frost, IEEE Transactions on Biomedical Engineering, vol. 25, no. 49, 1978.

In relation to epilepsy, the documents, "The potential value of 3d accelerometry for detection of motor seizures in severe epilepsy," by T. Nijsen et al., Epilepsy and Behavior, vol. 7, 2005, and "Detection of subtle nocturnal motor activity from 3d accelerometry recordings in epilepsy patients," by T. Nijsen et al., IEEE Transactions on Biomedical Engineering, vol. 54, 2007, focus on the distinction between nocturnal movements and seizure movements. Thus sensors are attached to a patient to detect a period in which motor activity occurs. One of the assumptions of this system is that the person does not read or visit the bathroom while the system is active.

These systems are used to detect long periods of motor activity, and can therefore only operate in strictly controlled conditions; in the conditions of everyday life, their capacity to detect an epileptic seizure is very limited.

BRIEF SUMMARY

One object of the invention is to overcome the aforesaid problems, for example to improve the accuracy of detection of an epileptic seizure in a prone person.

According to one aspect of the invention, a system is proposed for detecting an epileptic seizure in a prone person, comprising:

- at least one motion sensor sensibly fastened to said person with at least one measurement axis;
- a first determination module for determining a first probability of at least a first state transition diagram of the nocturnal activity of a prone person with respect to data representing the measurement signals of the motion sensor, said first diagram comprising predetermined probabilities of oriented transitions between two different or identical states, the probabilities of the states of said first diagram being predetermined;
- a second determination module for determining a second probability of at least a second state transition diagram for an epileptic seizure with respect to data representing the measurement signals of the motion sensor, said second diagram comprising predetermined probabilities of oriented transitions between two different or identical states, the probabilities of the states of said second diagram being predetermined;
- an association module for associating a state of said person as a function of the probabilities of the measurement signals of the motion sensor;
- a first calculation module for calculating the relations ($\phi_1$, $\phi_2$) between the first probability and the second probability; and
- a detection module for detecting an epileptic seizure when at least one of said calculated relations ($\phi_1$, $\phi_2$) is below a threshold ($\lambda_1$, $\lambda_2$).

A system of this type can be used with greater reliability to detect an epileptic seizure in a prone person.

In one embodiment, at least one of said state transition diagrams is adapted to use a hidden Markov model.

A hidden Markov model is defined by two random processes, namely a first process, which is called "state" in the present application and which is not observed, or which in other words is hidden, and a second process, which is the observation whose probability density at a given instant depends on the value of the state at the same instant.

In this instance, a hidden Markov model is defined by:

- an unobserved discrete process called the state, which can take w values, for example five values (w=5) out of the following: a rest activity (state 1), a slight agitation activity (state 2), a tremor activity (state 3), an agitation activity (state 4) and a strong agitation activity (state 5). This variable or state is a first order Markov chain, and is therefore characterized by the probabilities of transition from one state to another. In this embodiment, a state transition diagram is defined by:
- the set of w states, where w is 5 in the described example
- the probabilities of transition from one state to another, also called state transition probabilities:

$$\{a_{i,j} = P(\text{State}=i|\text{State}=j)\}_{i,j \in [1,\ldots,w]^2}$$

a second observed process of the hidden Markov model is the multidimensional signal of representative data, or, in other words, the signal of characteristics extracted from the observed signal and having a probability density depending on the state (the hidden process) at a given instant. Let O(n) denote this multidimensional signal at the instant n, and let $\{b_i(O(n))=P(O(n)|State=i)\}_{i \in [1, \ldots, w]}$ denote the w probabilities associated with this signal, as a function of the underlying hidden state.

A hidden Markov model is defined by the set pair Model=$\{\{a_{i,j}\}_{i,j},\{b_i\}_i\}$. The match between the observed signal and a given model is evaluated by the following probability: $P(O(0), \ldots, O(N-1)|Model)$ This probability can be estimated by the conventional prior art methods as described in "*An introduction to hidden Markov models*" by L. R. Rabiner and B. H. Juang, IEEE ASSP Magazine, January 1986, and in the book "*Inference in Hidden Markov Models*" by Cappé, Moulines and Ryden, published by Springer, in the "*Springer series in statistics*".

A number of models or state transition diagrams are defined, corresponding to different relevant movements, for example the first nocturnal movement state transition diagram and two second state transition diagrams, for tonic seizure movements and clonic seizure movements.

In a tonic seizure, muscles contract and relax rapidly, creating tremors, while in a clonic seizure there is strong agitation with sudden large movements.

The various probabilities $J_k=P(O(0), \ldots, O(N-1)|Model_k)$ for a given set of observations are calculated. $Model_k$ represents the set of parameters describing model k. An alarm can be triggered if the probabilities associated with seizure models are greater, by an amount above a certain threshold, than the probabilities associated with movements of other kinds. In other words, an epileptic seizure is detected when at least one of the calculated relations is below a threshold, where a relation is the ratio of a first probability to a second probability.

If the set of models associated with epileptic seizure movements is denoted by C and the set of "normal" movements is denoted by N, an epileptic seizure is detected when the following condition is met:

$\exists i \in C$ such that $\forall j \in N, J_j/J_i < \lambda_{i,j}$ $\lambda_{i,j}$ being an ad hoc threshold.

In one embodiment, the system additionally comprises:
a filter for selecting, for each measurement axis of the motion sensor, high frequencies above a first threshold, and low frequencies below a second threshold which is lower than or equal to said first threshold;
second means for calculating a first value equal to a linear combination of the respective variations along each measurement axis, between two successive time intervals, of said low frequencies per time interval;
third means for calculating a second value equal to the mean of the energies, along each measurement axis, of said high frequencies;
third means for determining the probability of said first value defined by a normal centered Gaussian distribution; and
fourth means for determining the probability of said second value defined by a Chi 2 distribution with a degree of freedom equal to the number of measurement axes of the motion sensor taken into consideration;
said means of association being adapted to use the probabilities of said low and high frequencies. In other words, the means of association are adapted to use the probabilities relative to the first and second values, defined respectively by the third and fourth means of determination. These means of association can be used to assign a probability of occurrence to each state, as a function of the first value and the second value which are found, respectively, by the second and third means of calculation.

The accuracy of detection is thus improved at a lower cost. The multidimensional signal O(n) and the associated probabilities $\{b_i(O(n))=P(O(n)|State=i)\}_{i \in [1, \ldots, w]}$ are defined as follows, with w=5, for example. The signal O(n) of characteristics extracted from the signal is of dimension 2. Its first component x(n) is the first value. Its second component y(n) is the second value. Each new sample corresponds to a value calculated over a time interval which may be 1 s, corresponding to a sampling frequency of 1 Hz, but as a general rule the sampling frequency can vary from 0.1 to 10 Hz, and preferably from 0.5 Hz to 4 Hz. Experimental trials have shown that a frequency of 1 Hz is satisfactory.

For a given type of movement p, the probability of observation is defined thus: $P(O(n)|Movement\_p)=P_{LF}^{(p)}(x(n)) \cdot P_{HF}^{(p)}(y(n))$ $P_{LF}^{(p)}(x(n))$ is the probability density relative to the first value; x(n) is the movement p, where p is a natural integer which is, for example, in the range from 1 to 50, and typically from 3 to 30; and $P_{HF}^{(p)}(y(n))$ is the probability density relative to the second value y(n) corresponding to the movement p.

In one embodiment, the probability density of obtaining a pair of values for the low frequency component and the high frequency component is equal to the product of the probability density of obtaining the value for the low frequency component and the probability density of obtaining the value for the high frequency component, and therefore said probability densities $(P_{LF}(x), P_{HF}(x))$ are defined by the following expressions, for each type of movement p:

$$\begin{cases} P_{LF}^{(p)}(x(n)) = \dfrac{1}{\sqrt{2\pi}\,\sigma_x^{(p)}} \cdot e^{-\frac{x(n)^2}{2\sigma_x^{(p)2}}} \\ P_{HF}^{(p)}(y(n)) = \dfrac{1}{\sqrt{2^k}\,\sigma_y^{(p)k}\,\Gamma\left(\frac{k}{2}\right)} y(n)^{\frac{k}{2}-1} e^{-\frac{y(n)}{2\sigma_y^{(p)2}}} \end{cases}$$

in which:
k represents the degree of freedom of the high frequency component (HF) equal to the number of measurement axes of said motion sensor (CM) taken into consideration;

$\sigma_x^{(p)}$ represents the variance of x, representing a type of movement p;

$\sigma_y^{(p)}$ represents the mean of the square roots of the energies of the high frequency components of the measurement axes considered, representing a type of movement p;

n represents the sample index; and $\Gamma$ is the gamma function obeying the rule $$\Gamma\left(\frac{1}{2}\right) = \sqrt{\pi}, \Gamma(1) = 1$$

and $\Gamma(z+1)=z\Gamma(z)$ where z is real.

Thus the real probability densities of the observed signals are approximated by probability densities globally adapted to most of the movements.

The number of pairs $(\sigma_x^{(p)}, \sigma_y^{(p)})$ and the respective values of these pairs are selected so as to describe a sufficiently comprehensive quantity of movements. The states, identified by the index i, are then described as more or less probable movements, by the following model:

$$b_i(O(n)) = [x(n), y(n)]^T)$$

$$= \sum_p \alpha_{i,p} P(O(n) | \text{Movement\_p})$$

$$= \sum_p \alpha_{i,p} \frac{1}{\sqrt{2\pi}\, \sigma_x^{(p)}} \cdot e^{-\frac{x(n)^2}{2\sigma_x^{(p)2}}} \times \frac{1}{\sqrt{2^k}\, \sigma_y^{(p)k} \Gamma\left(\frac{k}{2}\right)} y(n)^{\frac{k}{2}-1} e^{-\frac{y(n)}{2\sigma_y^{(p)2}}}$$

The coefficients $\alpha_{i,p}$ comply with the following constraint:

$$\sum_p \alpha_{i,p} = 1.$$

Thus the probability densities associated with the states are described in a highly accurate way, and the observed signals are modeled in a reasonably detailed way. Thus, when the person is at rest, a brief jerk does not have a zero probability. A jerk may also occur if the person is in a tremor state. However, this elementary movement will last longer in this state. This model enables these subtleties to be taken into account.

For example, the number of pairs $(\sigma_x^{(p)}, \sigma_y^{(p)})$ is 18, enabling 18 movements to be described.

For example, said 18 pairs are obtained by combining the following values:
$\sigma_x[0]=5\times10^{-3}$, $\sigma_x[1]=1.8\times10^{-2}$, $\sigma_x[2]=3.5\times10^{-2}$, $\sigma_x[3]=5\times 0.510^{-2}$, $\sigma_x[4]=8\times10^{-2}$, $\sigma_x[5]=1\times10^{-1}$, and $\sigma_y[0]=1\times10^{-2}$, $\sigma_y[1]=3\times10^{-2}$, $\sigma_y[2]=8\times10^{-2}$.

If p is an index such that p=m+6n, the pairs $(\sigma_x^{(p)}, \sigma_y^{(p)})$ are defined as follows: $(\sigma_x^{(p)}, \sigma_y^{(p)}) = (\sigma_x[m], \sigma_y[n])$ In one embodiment, where 5 states are considered (w=5), said coefficients $\alpha_{i,p}$ are defined as below, varying equally from 0 to 17:

| $\alpha_{i,p}$ | i = 1 (rest) | i = 2 (slight agitation) | i = 3 (tremors) | i = 4 (agitation) | i = 5 (strong agitation) |
|---|---|---|---|---|---|
| p = 0 | 0.2564 | 0 | 0 | 0 | 0 |
| 1 | 0.0513 | 0.0526 | 0 | 0 | 0 |
| 2 | 0.02564 | 0 | 0.04 | 0 | 0 |
| 3 | 0.2564 | 0.1579 | 0.04 | 0 | 0 |
| 4 | 0.0513 | 0.2632 | 0.16 | 0 | 0 |
| 5 | 0 | 0.0526 | 0.20 | 0 | 0 |
| 6 | 0.2564 | 0.1579 | 0.04 | 0 | 0 |
| 7 | 0.0513 | 0.2632 | 0.16 | 0.0926 | 0 |
| 8 | 0 | 0.0526 | 0.20 | 0.0926 | 0 |
| 9 | 0.0256 | 0 | 0 | 0.0370 | 0 |
| 10 | 0 | 0 | 0 | 0.1852 | 0 |
| 11 | 0 | 0 | 0.16 | 0.1852 | 0 |
| 12 | 0.0256 | 0 | 0 | 0.037 | 0.0556 |
| 13 | 0 | 0 | 0 | 0.1852 | 0.0556 |
| 14 | 0 | 0 | 0 | 0.1852 | 0.0556 |
| 15 | 0 | 0 | 0 | 0 | 0.2778 |
| 16 | 0 | 0 | 0 | 0 | 0.2778 |
| 17 | 0 | 0 | 0 | 0 | 0.2778 |

In one embodiment, the first state transition diagram for general nocturnal activity is defined as follows. $\alpha_{i,j}^n$ represents the probability of transition from state i to state j, P(State=i|State=j), for the n-th state transition diagram.

| $a_{i,j}^{(1)}$ | i = 1 | i = 2 | i = 3 | i = 4 | i = 5 |
|---|---|---|---|---|---|
| j = 1 | 0.9 | 0.025 | 0.025 | 0.025 | 0.025 |
| j = 2 | 0.025 | 0.9 | 0.025 | 0.025 | 0.025 |
| j = 3 | 0.025 | 0.025 | 0.9 | 0.025 | 0.025 |
| j = 4 | 0.025 | 0.025 | 0.025 | 0.9 | 0.025 |
| j = 5 | 0.025 | 0.025 | 0.025 | 0.025 | 0.9 |

In one embodiment, a second state transition diagram corresponding to an epileptic seizure with clonic manifestations is defined thus:

| $a_{i,j}^{(2)}$ | i = 1 | i = 2 | i = 3 | i = 4 | i = 5 |
|---|---|---|---|---|---|
| j = 1 | 0 | 0.3 | 0.7 | 0 | 0 |
| j = 2 | 0 | 0.9 | 0.1 | 0 | 0 |
| j = 3 | 0 | 0.1 | 0.9 | 0 | 0 |
| j = 4 | 0 | 0.3 | 0.7 | 0 | 0 |
| j = 5 | 0 | 0.3 | 0.7 | 0 | 0 |

In one embodiment, a second state transition diagram for an epileptic seizure with tonic manifestations is defined thus:

| $a_{i,j}^{(3)}$ | i = 1 | i = 2 | i = 3 | i = 4 | i = 5 |
|---|---|---|---|---|---|
| j = 1 | 0 | 0 | 0.7 | 0 | 0.3 |
| j = 2 | 0 | 0 | 0.7 | 0 | 0.3 |
| j = 3 | 0 | 0 | 0.9 | 0 | 0.1 |
| j = 4 | 0 | 0 | 0.7 | 0 | 0.3 |
| j = 5 | 0 | 0 | 0.3 | 0 | 0.7 |

In one embodiment, said second means of determination are adapted to determine a second probability of a second state transition diagram for an epileptic seizure with clonic manifestations and of a second state transition diagram for an epileptic seizure with tonic manifestations. Tonic manifestations include tremors, and clonic manifestations include agitation.

In one embodiment, the states and the probabilities of the states are identical for the first state transition diagram and for the second state transition diagrams.

Thus the process of implementation is simplified.

In this way, three state transition diagrams of signals are defined with the five states (rest, slight agitation, tremor, agitation, strong agitation). A first of these diagrams describing "general" nocturnal activity, a second describing motor manifestations of tonic epileptic seizures (with tremors) and a third describing motor manifestations of clonic epileptic seizures (with agitation).

In one embodiment, there is only one first state transition diagram, corresponding to general nocturnal activity, defined thus:

| $a_{i,j}^{(1)}$ | i = 1 | i = 2 | i = 3 | i = 4 | i = 5 |
|---|---|---|---|---|---|
| j = 1 | 0.9 | 0.025 | 0.025 | 0.025 | 0.025 |
| j = 2 | 0.025 | 0.9 | 0.025 | 0.025 | 0.025 |
| j = 3 | 0.025 | 0.025 | 0.9 | 0.025 | 0.025 |
| j = 4 | 0.025 | 0.025 | 0.025 | 0.9 | 0.025 |
| j = 5 | 0.025 | 0.025 | 0.025 | 0.025 | 0.9 |

In one embodiment, a second state transition diagram corresponding to an epileptic seizure with clonic manifestations is defined thus:

| $a_{i,j}^{(2)}$ | i = 1 | i = 2 | i = 3 | i = 4 | i = 5 |
|---|---|---|---|---|---|
| j = 1 | 0 | 0.3 | 0.7 | 0 | 0 |
| j = 2 | 0 | 0.9 | 0.1 | 0 | 0 |
| j = 3 | 0 | 0.1 | 0.9 | 0 | 0 |
| j = 4 | 0 | 0.3 | 0.7 | 0 | 0 |
| j = 5 | 0 | 0.3 | 0.7 | 0 | 0 |

In one embodiment, another second state transition diagram for an epileptic seizure with tonic manifestations is defined thus:

| $a_{i,j}^{(3)}$ | i = 1 | i = 2 | i = 3 | i = 4 | i = 5 |
|---|---|---|---|---|---|
| j = 1 | 0 | 0 | 0.7 | 0 | 0.3 |
| j = 2 | 0 | 0 | 0.7 | 0 | 0.3 |
| j = 3 | 0 | 0 | 0.9 | 0 | 0.1 |
| j = 4 | 0 | 0 | 0.7 | 0 | 0.3 |
| j = 5 | 0 | 0 | 0.3 | 0 | 0.7 |

Thus, the three models are defined with the three state transition diagrams (the first state transition diagram for general nocturnal activity and the two second state transition diagrams for an epileptic seizure with clonic and tonic manifestations respectively), the five defined states, the multidimensional signal O(n) and the associated probabilities $\{b_i(O(n))=P(O(n)|State=i)\}_{i \in [1,\ldots,5]}$.

Thus the process of implementation is simplified.

For a given observation, corresponding to a time interval ranging from several seconds to several minutes, for example 45 s, corresponding to N measured signals O(n), with indices from O(0) to O(N−1), the following three probabilities are calculated:

$$J_1 = P(O(0), \ldots, O(N-1)|Model_1)$$

$$J_2 = P(O(0), \ldots, O(N-1)|Model_2)$$

$$J_3 = P(O(0), \ldots, O(N-1)|Model_3)$$

together with the following two ratios:

$$\varphi_1 = \frac{J_1}{J_2} \text{ and } \varphi_2 = \frac{J_1}{J_3}$$

As a general rule, $J_i$ represents the probability of the observations, given the model i. $J_i$ is close to 0 if the observation does not match the model i. Conversely, $J_i$ is close to 1 if the observation does match the model i.

An alarm is triggered if $\varphi_1 < \lambda_1$ or $\varphi_2 < \lambda_2$, where $\lambda_1$ and $\lambda_2$ are thresholds chosen on an ad hoc basis. For example, $\lambda_1 = 1 \times 10^{-2}$ and $\lambda_2 = 1 \times 10^{-4}$.

In one embodiment, the system also comprises alerting means adapted for providing a warning of the detection of an epileptic seizure.

These alerting means can alert persons in the vicinity or remotely, by using an audible or visual alert for example.

In one embodiment, said motion sensor comprises an accelerometer, a magnetometer or a gyrometer.

According to another aspect of the invention, a method is also proposed for detecting an epileptic seizure in a prone person, wherein:

a first probability of at least a first state transition diagram of the nocturnal activity of a prone person is determined, with respect to the measurement signals of a motion sensor with at least one measurement axis having fastening means for securing said motion sensor to said person, said first diagram comprising predetermined probabilities of oriented transitions between two different or identical states, the probabilities of the states of said first diagram being predetermined;

a second probability of at least a second state transition diagram for an epileptic seizure is determined, with respect to the measurement signals of the motion sensor, a second diagram comprising predetermined probabilities of oriented transitions between two different or identical states, the probabilities of the states of said second diagram being predetermined;

a state of said person is associated as a function of the probabilities of the measurement signals of the motion sensor (CM);

relations of the second probability and the first probability are calculated; and an epileptic seizure is detected when at least one of said calculated relations is below a threshold.

BRIEF DESCRIPTION OF THE DRAWINGS

The invention will be more clearly understood by the examination of a number of embodiments described by way of non-limiting examples and illustrated in the attached drawings, in which.

DETAILED DESCRIPTION OF THE PREFERRED EMBODIMENTS

Figure 1:
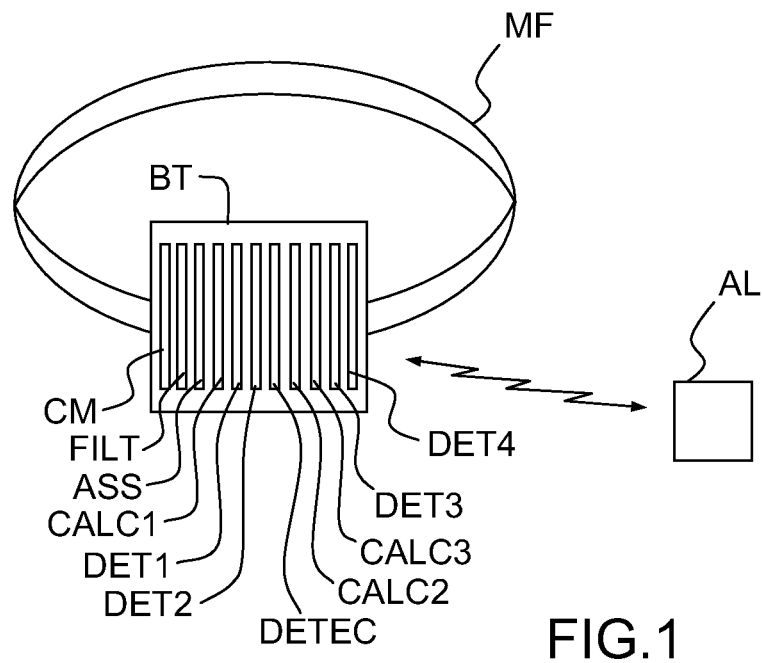
FIGS. 1 and 2 show two exemplary embodiments of a system for detecting an epileptic seizure in a prone person, according to one aspect of the invention.

FIG. 1 shows a system for detecting an epileptic seizure in a prone person, comprising at least one motion sensor CM with at least one measurement axis having fastening elements MF, comprising for example an elastic element, for securing a casing BT comprising the motion sensor CM to said person. The motion sensor CM can be an accelerometer, a magnetometer or a gyrometer, with one, two or three measurement axes. Clearly, the system can comprise a plurality of motion sensors CM.

The system comprises an association module ASS for associating a state of said person as a function of the probabilities of the measurement signals of the motion sensor CM, and a first determination module DET1 for determining a first probability of a first state transition diagram of the nocturnal activity of a prone person with respect to data representing the measurement signals of the motion sensor CM. The first diagram comprises predetermined probabilities of oriented transitions between two different or identical states, the probabilities of the states of said first diagram being predetermined.

The system also comprises a second determination module DET2 for determining a second probability of at least one second state transition diagram for an epileptic seizure with respect to data representing the measurement signals of the motion sensor CM. A second diagram comprises predetermined probabilities of oriented transitions between two different or identical states, the probabilities of the states of said second diagram being predetermined.

The system also comprises a first calculation module CALC1 for calculating the relations of the first probability and the second probability, and a module DETEC for detecting an epileptic seizure when at least one of said calculated relations is below a threshold.

In the remainder of the description, it is assumed, by way of example, that the second determination module DET2 uses one second state transition diagram for an epileptic seizure with clonic manifestations and one second state transition diagram for an epileptic seizure with tonic manifestations.

The system can include an alert or alarm module AL for providing a warning of the detection of an epileptic seizure remotely or in the vicinity, enabling people to intervene.

Figure 2:
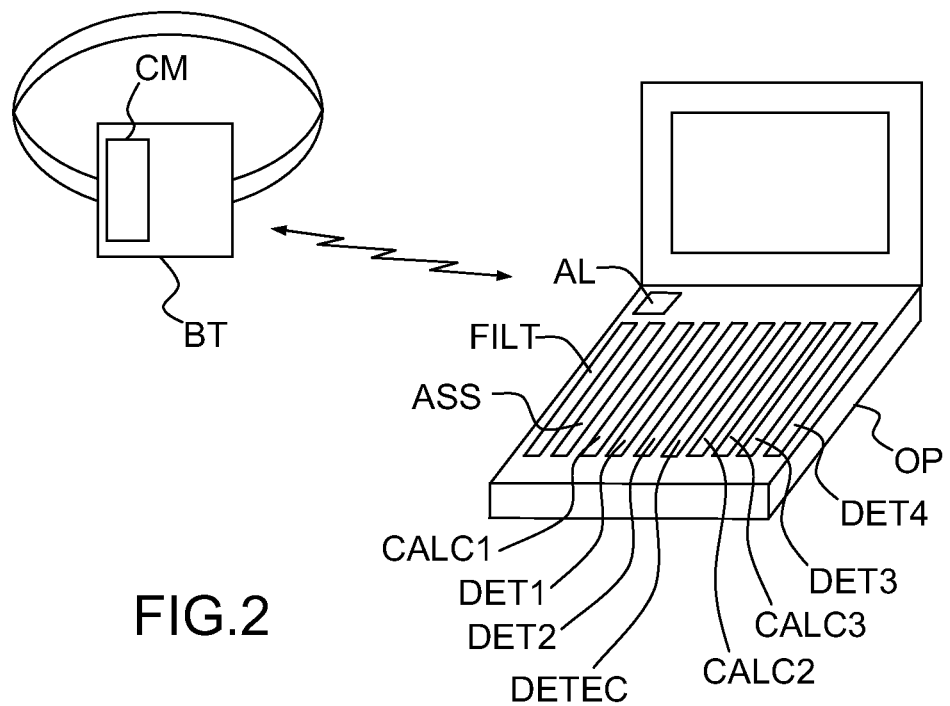

In a variant, as shown in FIG. 2, numerous elements may be included in a portable computer OP, for example, instead of in the casing BT as shown in FIG. 1.

The first state transition diagram of the nocturnal activity of a prone person can have the following probabilities of transitions between two of said five states:

| $a_{i,j}^{(1)}$ | i = 1 | i = 2 | i = 3 | i = 4 | i = 5 |
|---|---|---|---|---|---|
| j = 1 | 0.9 | 0.025 | 0.025 | 0.025 | 0.025 |
| j = 2 | 0.025 | 0.9 | 0.025 | 0.025 | 0.025 |
| j = 3 | 0.025 | 0.025 | 0.9 | 0.025 | 0.025 |
| j = 4 | 0.025 | 0.025 | 0.025 | 0.9 | 0.025 |
| j = 5 | 0.025 | 0.025 | 0.025 | 0.025 | 0.9 |

A first example of a second state transition diagram for an epileptic seizure with clonic manifestations can be defined by the following probabilities of transition:

| $a_{i,j}^{(2)}$ | i = 1 | i = 2 | i = 3 | i = 4 | i = 5 |
|---|---|---|---|---|---|
| j = 1 | 0 | 0.3 | 0.7 | 0 | 0 |
| j = 2 | 0 | 0.9 | 0.1 | 0 | 0 |
| j = 3 | 0 | 0.1 | 0.9 | 0 | 0 |
| j = 4 | 0 | 0.3 | 0.7 | 0 | 0 |
| j = 5 | 0 | 0.3 | 0.7 | 0 | 0 |

A second example of a second state transition diagram for an epileptic seizure with tonic manifestations can be defined by the following probabilities of transition:

| $a_{i,j}^{(3)}$ | i = 1 | i = 2 | i = 3 | i = 4 | i = 5 |
|---|---|---|---|---|---|
| j = 1 | 0 | 0 | 0.7 | 0 | 0.3 |
| j = 2 | 0 | 0 | 0.7 | 0 | 0.3 |
| j = 3 | 0 | 0 | 0.9 | 0 | 0.1 |
| j = 4 | 0 | 0 | 0.7 | 0 | 0.3 |
| j = 5 | 0 | 0 | 0.3 | 0 | 0.7 |

Based on the measurement signals of the motion sensor CM, the association module ASS identifies the state of said person among the set of states. The first determination module DET1 determines a first probability of the first state transition diagram with respect to data representing the measurement signals of the motion sensor CM.

Additionally, the second determination module DET2 determines a second probability of the second state transition diagram for an epileptic seizure with clonic manifestations with respect to data representing the measurement signals of the motion sensor CM, and determines a second probability of the second state transition diagram for an epileptic seizure with tonic manifestations with respect to the measurement signals of the motion sensor CM.

The first calculation module CALC1 estimates the relation $\phi_1$ of the first probability of the first state transition diagram and the second probability of the second state transition diagram for an epileptic seizure with clonic manifestations, as well as the relation $\phi_2$ of the first probability of the first state transition diagram and the second probability of the second state transition diagram for an epileptic seizure with tonic manifestations.

The detection module DETEC detects an epileptic seizure when at least one of the two relations calculated by the first calculation module CALC1 is below a threshold $\lambda_1$ or $\lambda_2$ respectively.

In the remainder of the description, the examples described use the low frequency components LF and the high frequency components HF, and there are two motion sensors CM, in the form of two three-axis accelerometers, a first of which is fastened to one wrist of a user, while the second is fastened to the user's other wrist or to his chest. A computer OP, as shown for example in FIG. 2, receives and records the data, detects an epileptic seizure and triggers an alert if an epileptic seizure is detected. Additionally, the state transition diagrams which have been described are adapted so that each of them uses a hidden Markov model.

At least one of said state transition diagrams can be adapted to use a hidden Markov model. The system may also comprise a filter FILT for selecting, for each measurement axis of the motion sensor CM, high frequencies HF above a first threshold S1, and low frequencies LF below a second threshold S2 which is lower than or equal to said first threshold S1. The system may also comprise a second calculation module CALC2 for calculating a first value x equal to a linear combination of the respective variations along each measurement axis, between two successive time intervals, of the low frequencies LF per time interval n, and may comprise a third calculation module CALC3 for calculating a second value y equal to the mean of the energies, along each measurement axis, of the high frequencies HF. Additionally, the system may comprise a third determination module DET3 for determining the probability PLF(x) of said first value x defined by a normal centered Gaussian distribution, and a fourth determination module DET4 for determining the probability PHF (x) of said second value y defined by a Chi 2 distribution with a degree of freedom equal to the number of measurement axes of the motion sensor CM taken into consideration. The means of association ASS are adapted to use the probabilities of the low and high frequencies LF and HF.

The probability density P(x(n),y(n)) of obtaining a pair of values (x(n), y(n)) for the low frequency component LF and the high frequency component HF being equal to the product of the probability density $P_{LF}(x)$ of obtaining the value x(n) for the low frequency component LF and the probability density $P_{HF}(x)$ of obtaining the value y(n) for the high frequency component HF, the probability densities $P_{LF}(x)$, $P_{HF}(x)$ being defined by the following expressions, for each type of movement p:

$$\begin{cases} P_{LF}^{(p)}(x(n)) = \dfrac{1}{\sqrt{2\pi}\,\sigma_x^{(p)}} \cdot e^{-\dfrac{x(n)^2}{2\sigma_x^{(p)2}}} \\ P_{HF}^{(p)}(y(n)) = \dfrac{1}{\sqrt{2^k}\,\sigma_y^{(p)k}\,\Gamma\left(\dfrac{k}{2}\right)} y(n)^{\frac{k}{2}-1} e^{-\dfrac{y(n)}{2\sigma_y^{(p)2}}} \end{cases}$$

wherein:
  k represents the degree of freedom of the high frequency component (HF) equal to the number of measurement axes of said motion sensor (CM) taken into consideration;
  $\sigma_x^{(p)}$ represents the variance of x, representing a type of movement p;
  $\sigma_y^{(p)}$ represents the mean of the square roots of the energies of the high frequency components of the measurement axes considered, representing a type of movement p;

n represents the sample index; and
Γ is the gamma function obeying the rule $$\Gamma\left(\frac{1}{2}\right) = \sqrt{\pi}, \Gamma(1) = 1$$

and Γ(z+1)=zΓ(z) where z is real.

Thus the present invention can significantly improve the detection of an epileptic seizure in a prone person, at a lower cost.

The invention claimed is:

1. A system for detecting an epileptic seizure in a prone person comprising:
   at least one motion sensor configured to couple to a person, the at least one motion sensor having at least one measurement axis; and
   a computing device configured to perform steps comprising:
      a first determination of a first probability of at least a first state transition diagram of nocturnal activity of a prone person with respect to data representing measurement signals of the motion sensor, said first diagram comprising predetermined probabilities of oriented transitions between two different or identical states, the probabilities of the states of said first diagram being predetermined;
      a second determination of a second probability of at least a second state transition diagram for an epileptic seizure with respect to data representing the measurement signals of the motion sensor, said second diagram comprising predetermined probabilities of oriented transitions between two different or identical states, the probabilities of the states of said second diagram being predetermined;
      associating a state of said person as a function of probabilities of the measurement signals of the motion sensor, said probabilities being calculated separately for high frequencies of the measurement signals above a first frequency threshold, and for low frequencies of the measurement signals below a second frequency threshold, the second frequency threshold being equal to or less than the first frequency threshold;
      calculating relations between the first probability and the second probability; and
      detecting an epileptic seizure when at least one of said calculated relations is below a threshold.

2. The system of claim 1, wherein at least one of said state transition diagrams is adapted to use a hidden Markov model.

3. The system of claim 2, wherein computing device is further configured to perform steps comprising:
   filtering, for each measurement axis of the motion sensor, high frequencies above the first frequency threshold, and low frequencies below the second frequency threshold;
   calculating a first value x equal to a linear combination of respective variations along each measurement axis, between two successive time intervals, of said low frequencies per time interval n;
   calculating a second value y equal to a mean of energies, along each measurement axis, of said high frequencies;
   determining a probability $P_{LF}(x)$ of said first value x defined by a normal centered Gaussian distribution; and
   determining a probability $P_{HF}(x)$ of said second value y defined by a Chi-squared distribution with a degree of freedom equal to the number of measurement axes of the motion sensor taken into consideration.

4. The system of claim 3, wherein a probability density P(x(n),y(n)) of obtaining a pair of values (x(n), y(n)) for the low frequency component and the high frequency component being equal to a product of the probability density $P_{LF}(x)$ of obtaining a value x(n) for the low frequency component and a probability density $P_{HF}(x)$ of obtaining a value y(n) for the high frequency component, said probability densities $P_{LF}(x)$ and $P_{HF}(x)$ being defined by the following expressions:

$$\begin{cases} P_{LF}^{(p)}(x(n)) = \frac{1}{\sqrt{2\pi}\,\sigma_x^{(p)}} \cdot e^{-\frac{x(n)^2}{2\sigma_x^{(p)2}}} \\ P_{HF}^{(p)}(y(n)) = \frac{1}{\sqrt{2^k}\,\sigma_y^{(p)k}\,\Gamma\left(\frac{k}{2}\right)} y(n)^{\frac{k}{2}-1} e^{-\frac{y(n)}{2\sigma_y^{(p)2}}} \end{cases}$$

wherein:
k corresponds to a degree of freedom of the high frequency component equal to the number of measurement axes of said motion sensor taken into consideration;
$\sigma_x^{(p)}$ corresponds to a variance of x, representing a type of movement p;
$\sigma_y^{(p)}$ corresponds to a mean of the square roots of the energies of the high frequency components of the measurement axes considered, representing a type of movement p;
n corresponds to a sample index; and
Γ is a gamma function obeying $$\Gamma\left(\frac{1}{2}\right) = \sqrt{\pi}, \Gamma(1) = 1$$

and Γ(z+1)=zΓ(z) where z is real.

5. The system of claim 2, wherein said hidden Markov model comprises no more than five states chosen from a group consisting of a rest activity, a slight agitation activity, a tremor activity, an agitation activity and a strong agitation activity.

6. The system of claim 2, wherein the probabilities of the states of said state transition diagrams are defined by the following relation:

$$b_i(O(n) = [x(n), y(n)]^T) = \sum_p \alpha_{i,p} \frac{1}{\sqrt{2\pi}\,\sigma_x^{(p)}} \cdot e^{-\frac{x(n)^2}{2\sigma_x^{(p)2}}} \times \frac{1}{\sqrt{2^k}\,\sigma_y^{(p)k}\,\Gamma\left(\frac{k}{2}\right)} y(n)^{\frac{k}{2}-1} e^{-\frac{y(n)}{2\sigma_y^{(p)2}}}$$

wherein a value of a pair of a variance $\sigma_x^{(p)}$ of the first value x and a variance $\sigma_y^{(p)}$ of the second value y ($\sigma_x^{(p)}$, $\sigma_y^{(p)}$) depends on a description of a movement, and coefficients $\alpha_{i,p}$ comply with the following constraint:

$$\sum_p \alpha_{i,p} = 1.$$

7. The system of claim 1, wherein said second determination further determines a second probability of a second state transition diagram for an epileptic seizure with clonic manifestations and of a second state transition diagram for an epileptic seizure with tonic manifestations.

8. The system of claim 1, wherein the states and the probabilities of the states are identical for the first state transition diagram and for the second state transition diagrams.

9. The system of claim 6, wherein there are 18 of said pairs of variances ($\sigma_x^{(i)}, \sigma_y^{(i)}$), which are obtained by a combination of the following values:

$\sigma_x[0]=5\times10^{-3}$, $\sigma_x[1]=1.8\times10^{-2}$, $\sigma_x[2]=3.5\times10^{-2}$, $\sigma_x[3]=5\times0.510^{-2}$, $\sigma_x[4]=8\times10^{-2}$, $\sigma_x[5]=1\times10^{-1}$, and $\sigma_y[0]=1\times10^{-2}$, $\sigma_y[1]=3\times10^{-2}$, $\sigma_y[2]=8\times10^{-2}$.

10. The system of claim 9, wherein said coefficients $\alpha_{i,p}$ are defined as follows, for a pair of variances ($\sigma_x^{(p)}[m], \sigma_y^{(p)}[n]$), where p is an index such that p=m+6n, varying from 0 to 17 for the 18 pairs ($\sigma_x^{(p)}, \sigma_y^{(p)}$):

| $\alpha_{i,p}$ | i = 1 (rest) | i = 2 (slight agitation) | i = 3 (tremors) | i = 4 (agitation) | i = 5 (strong agitation) |
|---|---|---|---|---|---|
| p = 0 | 0.2564 | 0 | 0 | 0 | 0 |
| 1 | 0.0513 | 0.0526 | 0 | 0 | 0 |
| 2 | 0.02564 | 0 | 0.04 | 0 | 0 |
| 3 | 0.2564 | 0.1579 | 0.04 | 0 | 0 |
| 4 | 0.0513 | 0.2632 | 0.16 | 0 | 0 |
| 5 | 0 | 0.0526 | 0.20 | 0 | 0 |
| 6 | 0.2564 | 0.1579 | 0.04 | 0 | 0 |
| 7 | 0.0513 | 0.2632 | 0.16 | 0.0926 | 0 |
| 8 | 0 | 0.0526 | 0.20 | 0.0926 | 0 |
| 9 | 0.0256 | 0 | 0 | 0.0370 | 0 |
| 10 | 0 | 0 | 0 | 0.1852 | 0 |
| 11 | 0 | 0 | 0.16 | 0.1852 | 0 |
| 12 | 0.0256 | 0 | 0 | 0.037 | 0.0556 |
| 13 | 0 | 0 | 0 | 0.1852 | 0.0556 |
| 14 | 0 | 0 | 0 | 0.1852 | 0.0556 |
| 15 | 0 | 0 | 0 | 0 | 0.2778 |
| 16 | 0 | 0 | 0 | 0 | 0.2778 |
| 17 | 0 | 0 | 0 | 0 | 0.2778 |

11. The system of claim 10, wherein a first state transition diagram of general nocturnal activity is defined by the following matrix:

| $a_{i,j}^{(1)}$ | i = 1 | i = 2 | i = 3 | i = 4 | i = 5 |
|---|---|---|---|---|---|
| j = 1 | 0.9 | 0.025 | 0.025 | 0.025 | 0.025 |
| j = 2 | 0.025 | 0.9 | 0.025 | 0.025 | 0.025 |
| j = 3 | 0.025 | 0.025 | 0.9 | 0.025 | 0.025 |
| j = 4 | 0.025 | 0.025 | 0.025 | 0.9 | 0.025 |
| j = 5 | 0.025 | 0.025 | 0.025 | 0.025 | 0.9 |

12. The system of claim 10, wherein a second state transition diagram for an epileptic seizure with clonic manifestations is defined by the following matrix:

| $a_{i,j}^{(2)}$ | i = 1 | i = 2 | i = 3 | i = 4 | i = 5 |
|---|---|---|---|---|---|
| j = 1 | 0 | 0.3 | 0.7 | 0 | 0 |
| j = 2 | 0 | 0.9 | 0.1 | 0 | 0 |
| j = 3 | 0 | 0.1 | 0.9 | 0 | 0 |
| j = 4 | 0 | 0.3 | 0.7 | 0 | 0 |
| j = 5 | 0 | 0.3 | 0.7 | 0 | 0 |

13. The system of claim 10, wherein a second state transition diagram for an epileptic seizure with tonic manifestations is defined by the following matrix:

| $a_{i,j}^{(3)}$ | i = 1 | i = 2 | i = 3 | i = 4 | i = 5 |
|---|---|---|---|---|---|
| j = 1 | 0 | 0 | 0.7 | 0 | 0.3 |
| j = 2 | 0 | 0 | 0.7 | 0 | 0.3 |
| j = 3 | 0 | 0 | 0.9 | 0 | 0.1 |
| j = 4 | 0 | 0 | 0.7 | 0 | 0.3 |
| j = 5 | 0 | 0 | 0.3 | 0 | 0.7 |

14. The system of claim 1, further comprising an alarm configured to provide a warning of the detection of an epileptic seizure.

15. The system of claim 1, wherein said motion sensor comprises an accelerometer, a magnetometer or a gyrometer.

16. A method for detecting an epileptic seizure in a prone person, the method comprising:
  obtaining measurement signals from a motion sensor configured to be coupled to a prone person, the motion sensor having at least one measurement axis;
  determining a first probability of at least a first state transition diagram of nocturnal activity of the prone person, with respect to the measurement signals of the motion sensor, said first diagram comprising predetermined probabilities of oriented transitions between two different or identical states, the probabilities of the states of said first diagram being predetermined;
  determining a second probability of at least a second state transition diagram for an epileptic seizure, with respect to the measurement signals of the motion sensor, where said second diagram comprises predetermined probabilities of oriented transitions between two different or identical states, the probabilities of the states of said second diagram being predetermined;
  associating a state of said person as a function of probabilities of the measurement signals of the motion sensor, said probabilities being calculated separately for high frequencies of the measurement signals above a first frequency threshold, and for low frequencies of the measurement signals below a second frequency threshold, the second frequency threshold being equal to or less than the first frequency threshold;
  calculating relations of the first probability and the second probability; and
  detecting an epileptic seizure when at least one of said calculated relations is below a threshold.

* * * * *